(12) United States Patent
Albu

(10) Patent No.: US 9,806,627 B2
(45) Date of Patent: Oct. 31, 2017

(54) SYSTEM INCLUDING POWER SUPPLY AND POWER CONVERTER FOR PROVIDING AC POWER TO MEDICAL DEVICES

(71) Applicant: ST. JUDE MEDICAL, ATRIAL FIBRILLATION DIVISION, INC., St. Paul, MN (US)

(72) Inventor: Ryan M. Albu, Minneapolis, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 609 days.

(21) Appl. No.: 14/319,385

(22) Filed: Jun. 30, 2014

(65) Prior Publication Data

US 2015/0008739 A1 Jan. 8, 2015

Related U.S. Application Data

(60) Provisional application No. 61/842,139, filed on Jul. 2, 2013.

(51) Int. Cl.
*H02J 3/00* (2006.01)
*H02M 5/458* (2006.01)
(Continued)

(52) U.S. Cl.
CPC ......... *H02M 5/458* (2013.01); *A61B 18/1206* (2013.01); *A61B 18/1233* (2013.01); *A61B 2018/00351* (2013.01); *A61B 2018/00577* (2013.01); *A61B 2018/1286* (2013.01); *H02M 7/4807* (2013.01); *H02M 2001/007* (2013.01); *H02M 2001/008* (2013.01); *Y10T 307/344* (2015.04); *Y10T 307/406* (2015.04)

(58) Field of Classification Search
CPC .......... H02M 5/458; H02M 2001/008; H02M 2001/007; H02M 7/4807; Y10T 307/344; Y10T 307/406
USPC .......................................................... 307/23
See application file for complete search history.

(56) References Cited

U.S. PATENT DOCUMENTS 6,566,855 B1 * 5/2003 Nguyen ............... G01R 19/252
324/117 H
7,622,823 B2 * 11/2009 Morishima ............. H02J 9/062
307/66

(Continued)

OTHER PUBLICATIONS

Bell et al., "Topology Key to Power Density in Isolated DC-DC Converters"; Power Electronics Technology, 2011; pp. 16-20.

*Primary Examiner* — Jared Fureman
*Assistant Examiner* — Michael Warmflash
(74) *Attorney, Agent, or Firm* — Armstrong Teasdale LLP

(57) ABSTRACT

Low leakage current power supply methods, systems, and apparatus are described. In one example, a medical system includes a plurality of medical devices and a power supply configured to provide alternating current (AC) power to the plurality of medical devices. The power supply includes an input configured to receive AC power from an AC power source, an isolated switching power converter coupled to the input to receive the AC power and output AC power, a controller coupled to the isolated switching power converter and configured to control operation of the isolated switching power converter, and an output coupled to the isolated switching power converter to provide the AC power output.

12 Claims, 6 Drawing Sheets

(51) Int. Cl.
  *A61B 18/12* (2006.01)
  *H02M 7/48* (2007.01)
  *H02M 1/00* (2006.01)
  *A61B 18/00* (2006.01)

(56) References Cited

U.S. PATENT DOCUMENTS

| | | |
|---|---|---|
| 8,118,775 B2 | 2/2012 | Grunewald et al. |
| 2002/0032439 A1* | 3/2002 | Hareyama .......... A61B 18/1206 606/38 |
| 2011/0305049 A1* | 12/2011 | Raptis .................... H02J 9/062 363/34 |
| 2012/0195078 A1* | 8/2012 | Levin ................ A61B 18/1233 363/50 |

* cited by examiner

SYSTEM INCLUDING POWER SUPPLY AND POWER CONVERTER FOR PROVIDING AC POWER TO MEDICAL DEVICES

CROSS-REFERENCE TO RELATED APPLICATIONS

This application claims priority to provisional application Ser. No. 61/842,139, filed Jul. 2, 2013, the entire specification of which is incorporated herein.

FIELD OF THE DISCLOSURE

The present disclosure relates generally to low leakage current power supply methods, systems, and apparatuses. More particularly, the present disclosure relates to methods, systems, and apparatuses for supplying power, and particularly AC power, to medical equipment with low overall patient leakage current levels such that the systems and apparatuses meet required safety and regulatory guidelines.

BACKGROUND OF THE DISCLOSURE

Many types of medical equipment are subject to various safety regulations and/or requirements to ensure patient safety standards are met. One type of safety regulation to which electrically powered medical equipment is subject is patient leakage limitations. For example, IEC60601-1 $3^{rd}$ edition (Section 8.7 entitled: Leakage Currents and Patient Auxiliary Currents) testing defines the testing and current leakage limits for a type CF (cardiac floating) Applied part. As part of this standard, total patient leakage current is limited to 100 microamps ($\mu$A), and the single fault condition patient leakage current is limited to 50 $\mu$A. Individual items of medical equipment are typically designed to meet these (and other) safety limitations such that they can be safely incorporated and used with various medical equipment systems.

In some environments, it is not uncommon to combine multiple items of medical equipment together in a medical cart or cabinet to form a consolidated medical system that may optionally be portable to enhance usability. In the context of a cardiac electrophysiology laboratory, for example, it may be useful to organize the hardware used for performing electroanatomical mapping and ablation procedures into a single, medical cart or cabinet in order to reduce clutter and improve usability of the equipment in the laboratory. The consolidated medical system must still meet the applicable safety regulations and standards.

In many circumstances, an isolation transformer is inserted between the alternating current (AC) power source and one or more pieces of the equipment forming the consolidated medical system in order to reduce noise and leakage currents. Such isolation transformers, however, are often relatively large in size in order to handle the power requirements of all of the medical equipment in the consolidated system. The large surface area of such transformers allows for capacitive coupling of 60 hertz (Hz) fault power between the primary and secondary sides of the isolation transformer. This capacitive coupling can potentially result in the generation of leakage currents on the output side of the power supply, making it difficult to maintain the patient leakage current below the required maximum levels.

BRIEF SUMMARY OF THE DISCLOSURE

The present disclosure is generally directed to medical apparatuses and systems including an improved AC power supply configured to provide alternating current power to the system or apparatus. Also disclosed herein are methods of supplying improved alternating current power to a medical apparatus or system. The improved AC power supply is a low overall current leakage AC power supply that can be used in many types of electrical equipment, including medical equipment and devices such that the medical equipment and devices meet or exceed required safety guidelines.

In one aspect of the present disclosure, a medical system includes a plurality of medical devices and a power supply configured to provide alternating current (AC) power to the plurality of medical devices. The power supply includes an input configured to receive AC power from an AC power source, an isolated switching power converter coupled to the input to receive the AC power and output AC power, a controller coupled to the isolated switching power converter and configured to control operation of the isolated switching power converter, and an output coupled to the isolated switching power converter to provide the AC power output.

In another aspect of the present disclosure, a method of supplying alternating current (AC) power to a plurality of medical devices includes receiving AC power having a first frequency from an AC power source, rectifying the AC power to a direct current (DC) power at a first voltage, converting the DC power to a DC power at a second voltage greater than the first voltage, converting the DC power at the second voltage to a DC power at a third voltage less than the second voltage with an isolated DC to DC power converter at a switching frequency greater than the first frequency, and converting the DC power at the third voltage to an AC power output at the first frequency.

Another aspect of the present disclosure is a power supply for supplying alternating current (AC) power to a plurality of medical devices. The power supply includes an input configured to receive AC power from an AC power source, and an isolated switching power converter coupled to the input to receive the AC power and output AC power. The isolated switching power converter includes an AC to direct current (AC/DC) converter stage coupled to the input and configured to output DC power, and a DC to AC (DC/AC) converter stage coupled to the AC/DC converter and configured to receive the DC power output from the AC/DC converter and output AC power. The power supply further includes a controller coupled to the isolated switching power converter and configured to control operation of the isolated switching power converter, and an output coupled to the isolated switching power converter to provide the AC power output to the plurality of medical devices.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the drawings.

DETAILED DESCRIPTION OF THE DISCLOSURE

The present disclosure is generally directed to low leakage current power supply methods, systems, and apparatuses. More particularly, the present disclosure relates to methods, systems, and apparatuses for supplying power to medical equipment with low patient leakage current. In many embodiments, the medical equipment may include two or more separate pieces of medical equipment that are combined into a medical cart or medical cabinet that may, in some embodiments, be suitable for use in cardiac electrophysiology procedures such as cardiac electroanatomical mapping and ablation procedures. The medical cart or cabinet may, in some embodiments, be portable to enhance usability in various applications and/or at different locations. In some embodiments, the power supply for the medical cart or medical cabinet will have a total patient leakage current of 100 or less µA, or even less than 90 µA, or less than 80 µA, or less than 70 µA.

Embodiments of the present disclosure forego reliance solely on magnetics-only solutions that use a medical grade isolation transformer. Rather, the embodiments of the present disclosure generally include a medical grade CF rated alternating current (AC) to direct current (DC) power supply connected to a DC to AC power inverter. Some embodiments further employ an AC power conditioning stage to further reduce noise and leakage. Some embodiments of this disclosure take advantage of an isolated DC-DC switching converter topology that is switched at relatively high frequencies (e.g., 100 kHz to several MHz). By boosting the power from the 120 volt (V) or 240V input to a higher DC voltage, and then stepping the voltage down at a relatively high switching frequency, the size of the transformer(s) in the power supply are greatly reduced as compared to many magnetics only solutions that may be conventionally utilized. Specifically, by increasing the voltage, the current is reduced proportionally, reducing the size of the windings needed in the transformer. Moreover, the high switching frequency decreases the size of the transformer core that is needed. This leads to an overall reduction in the transformer size. The reduced surface area of the transformer reduces the capacitive coupling and 60 Hz leakage currents in the transformer. Furthermore, some embodiments described herein monitor the frequency of the input AC voltage and operate the power supply to output AC power with the same frequency. Some embodiments also shift the output AC power 180 degrees out of phase with the input power, which may further reduce leakage currents and biosignal noise.

Figure 1:
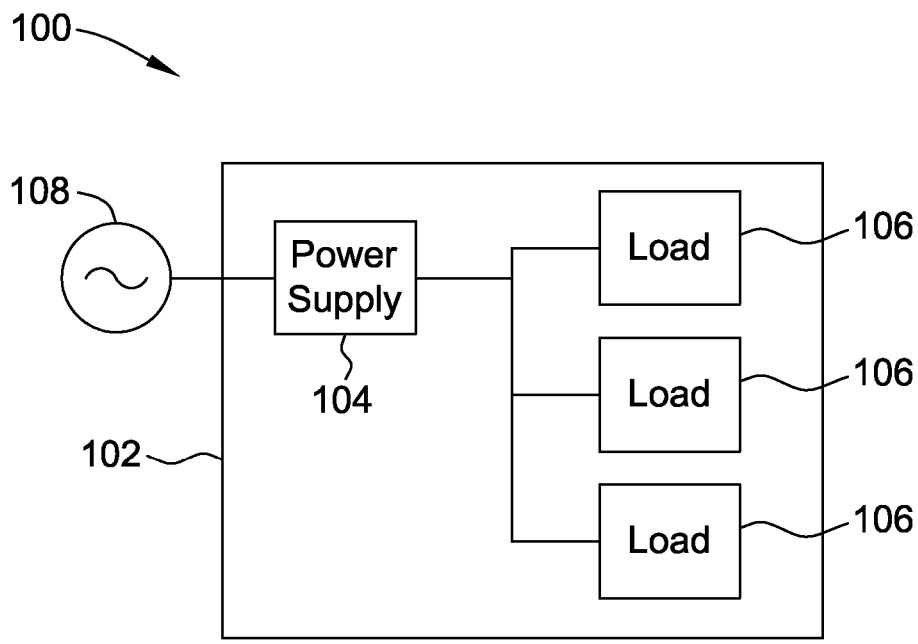
FIG. 1 is a block diagram of one embodiment of a medical system according to the present disclosure.

Referring now to the drawings and in particular to FIG. 1 in order to more fully describe the many embodiments of the present disclosure, a medical system 100 includes housing 102, power supply 104, and loads 106. The housing 102 supports and/or encloses the power supply 104 and the loads 106. In the exemplary embodiment, the housing 102 is a mobile medical cart. Alternatively, the housing 102 may be a stationary medical cart, mobile or stationary cabinet, an equipment rack, or any other suitable housing for use in a medical or related environment. The loads 106 are medical equipment (sometimes referred to herein as medical devices) forming a consolidated medical system. In one example medical system 100, loads 106 are cardiac electrophysiology equipment (e.g., a cardiac mapping system, a cardiac stimulator, an electrophysiology recording system, etc.) used as part of a cardiac electrophysiology system. Although three loads 106 are shown in FIG. 1, the medical system 100 may include more or fewer loads 106. The power supply 104 is an isolated alternating current (AC) to AC power supply coupled to an AC power source 108 and configured to provide power to the loads 106 with relatively low leakage current. More particularly, the power supply 104 is an isolated, switching power supply.

Figure 2:
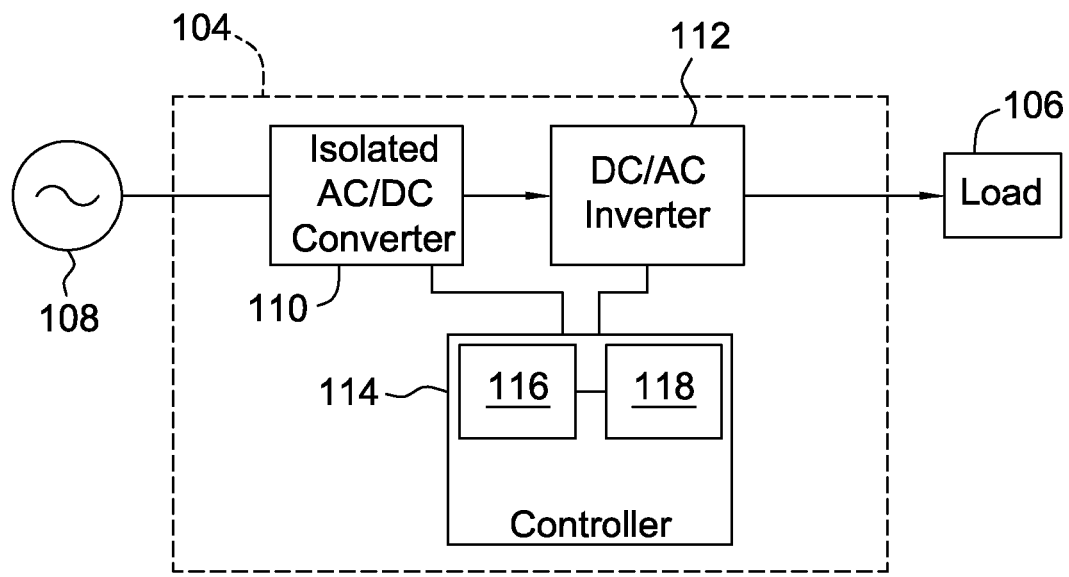
FIG. 2 is a block diagram of one embodiment of a power supply for use in the medical system shown in FIG. 1.

FIG. 2 is a block diagram of an exemplary embodiment of the power supply 104 coupled to the AC power source 108 and one load 106.

The power supply 104 includes an isolated AC to direct current (DC) converter 110 and a DC to AC converter 112. A controller 114 controls operation of the AC/DC converter 110 and the DC/AC converter 112 (sometimes referred to herein as an inverter).

The isolated AC/DC converter 110 is a switching power converter including at least one transformer (not shown in FIG. 2) to provide isolation between the input and the output of the isolated AC/DC converter 110. The isolated AC/DC converter 110 may be any suitable isolated power converter topology include, for example, a flyback converter, a forward converter, a full bridge converter, a half bridge converter, a push-pull converter, etc. In the exemplary embodiment, the AC/DC converter 110 generates a first DC voltage with a magnitude greater than the magnitude of the AC voltage input to the converter 110 from the AC power source, and then generates a second DC voltage with a magnitude less than the first DC voltage. In some embodiments, the AC input voltage is 110 VAC or 220 VAC and the second DC voltage is in a range from 3 Volts to 240 Volts. For example, the second DC voltage may be 12 Volts, 24 Volts, 48 Volts, or 100 Volts. Alternatively, the AC input voltage, the first DC voltage, and the second DC voltage may have any values that enable power supply 104 to function as described herein.

The DC/AC converter 112 converts the second DC voltage from the isolated AC/DC converter 110 to an AC voltage having about the same magnitude as the AC voltage received form the AC power source 108. The value of the AC voltage output from DC/AC converter 112 is independent from the DC voltage input to the DC/AC converter 112 (i.e., the second DC voltage). Further, the DC/AC converter 112 may be any high frequency inverter suitable for converting the DC output of the AC/DC converter 110 to an AC output. In the preferred embodiment, the AC output is a pure sine wave. However, in other embodiments, the AC output may be a square wave, a triangle wave, and/or any other waveform that enables power supply 104 to function as described herein.

By switching at high speeds (e.g., more than about 100 kHz) and using increased voltages (at correspondingly lower currents), the power supply 104 is operable with smaller transformers. Leakage current is generally proportional to transformer size, especially surface area. Because a smaller isolation transformer may be used in the isolated AC/DC converter 110, the surface area for capacitive coupling is reduced and the leakage current resulting from the isolated AC/DC converter 110 is reduced compared to designs including larger transformers.

Again referring to FIG. 2, the controller 114 includes a processor 116 and memory device 118 coupled to processor 116. The controller 114 is configured to control operation of the AC/DC converter 110 and the DC/AC converter 112 by suitable instructions stored, for example, in the memory device 118. Other suitable embodiments do not include processor 116 and/or memory device 118. The term "processor" refers herein generally to any programmable system including systems and microcontrollers, reduced instruction set circuits (RISC), application specific integrated circuits (ASIC), programmable logic circuits, field programmable gate array (FPGA), gate array logic (GAL), programmable array logic (PAL), digital signal processor (DSP), and any other circuit or processor capable of executing the functions described herein. The above examples are exemplary only, and thus are not intended to limit in any way the definition and/or meaning of the term "processor." Although a single processor is illustrated in FIG. 2, processor 116 may include more than one processor and the actions described herein may be shared by more than one processor. Moreover, although controller 114 is illustrated in FIG. 2 as a component of power supply 104, controller 114 may be a part of and/or shared with one or more other systems.

Memory device 118 stores program code and instructions, executable by processor 116. When executed by processor 116, the program code and instructions cause processor 116, and hence the controller 114, to operate as described herein. Memory device 118 may include, but is not limited to only include, non-volatile RAM (NVRAM), magnetic RAM (MRAM), ferroelectric RAM (FeRAM), read only memory (ROM), flash memory and/or Electrically Erasable Programmable Read Only Memory (EEPROM). Any other suitable magnetic, optical and/or semiconductor memory, by itself or in combination with other forms of memory, may be included in memory device 118. Memory device 118 may also be, or include, a detachable or removable memory, including, but not limited to, a suitable cartridge, disk, CD ROM, DVD or USB memory. Although illustrated separately from processor 116, memory device 118 may be integrated with processor 116 in other suitable embodiments of the present disclosure.

Figure 3:
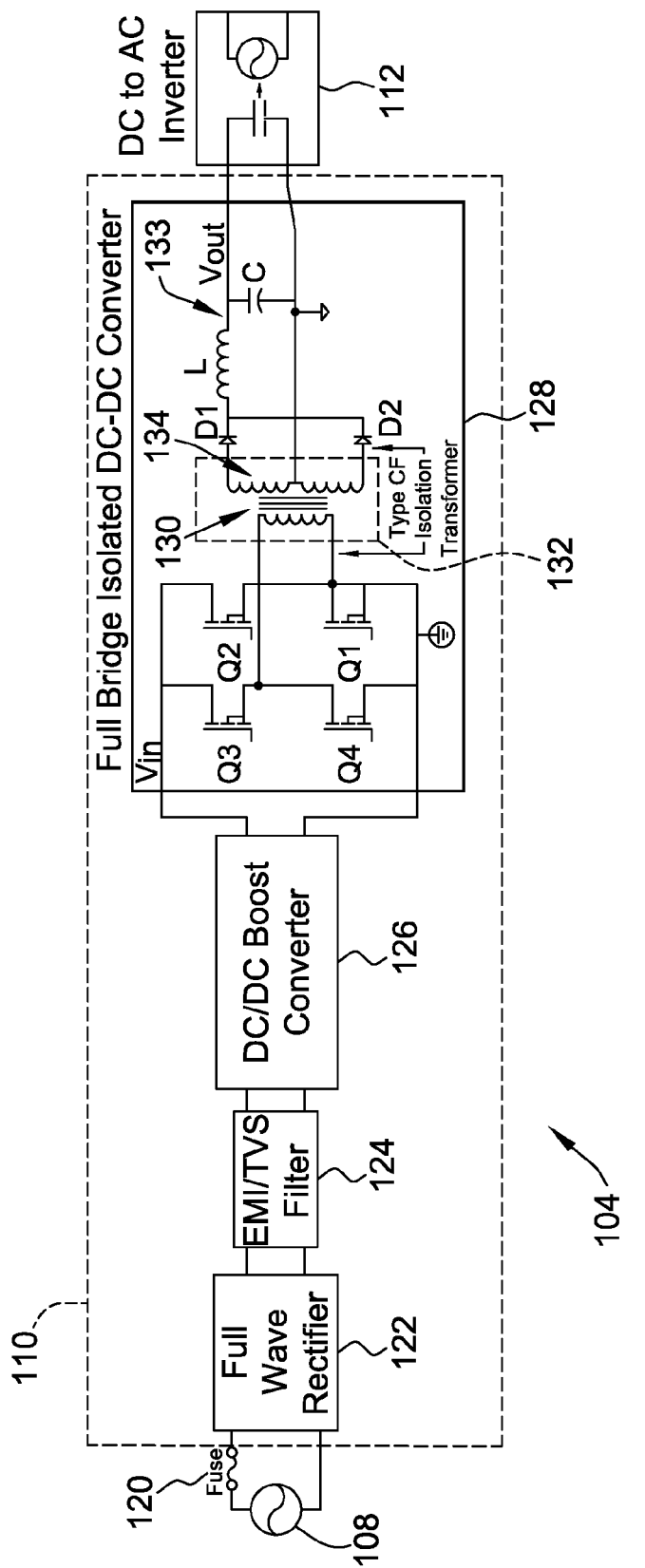
FIG. 3 is a diagram of another embodiment of a power supply for use in the medical system shown in FIG. 1.

Turning now to FIG. 3, there is shown a diagram of another exemplary power supply 104 including an isolated AC/DC converter 110 and a DC/AC converter 112. In one example medical system, the power supply 104 is an 800 volt-ampere (VA), 720 watt (W) power supply operable at a power factor of 0.9. The power supply is configured to operate with an input AC voltage between 85 and 264 volts root mean square (Vrms) and having a frequency between about 47 Hz and about 63 Hz. The AC power output of the power supply 104 is a 120 volt AC output with a frequency substantially the same as the frequency of the AC input voltage. The power supply has a single fault condition leakage current of less than 50 μA. In other embodiments, the single fault condition leakage current may be less than 45 μA, or 40 μA, or 35 μA, or 30 μA or 25 μA, or even 20 μA.

The isolated AC/DC converter 110 receives the AC input from the AC source 108 through a fuse 120 and outputs a DC output to the DC/AC converter 112. In the illustrated embodiment, the isolated AC/DC converter 110 is a multi-stage converter. A full wave rectifier 122 rectifies the AC voltage input to the AC/DC converter 110 to a substantially DC voltage. The rectified voltage passes through a filter 124 to a DC/DC converter stage 126. In some embodiments, for example, the filter 124 is an electromagnetic interference and transient voltage suppression (EMI/TVS) filter, and the DC/DC converter stage 126 is a boost converter 126. The controller 114 (shown in FIG. 2) controls operation of the boost converter 126 to produce a DC output voltage greater than the DC voltage input to the boost converter 126. Boost converters and their control are well known to those of ordinary skill in the art and will not be described in further detail herein.

The output of the boost converter 126 is input to an isolated DC/DC converter stage 128. In the exemplary embodiment, the isolated DC/DC converter stage is a full-bridge converter. In other embodiments, the isolated DC/DC converter stage 128 is any other suitable isolated DC/DC converter, such as a flyback converter, a forward converter, a half bridge converter, a push-pull converter, etc. The isolated DC/DC converter stage 128 includes four switches Q1-Q4 coupled to the primary winding 130 of transformer 132. In some embodiments, for example, the four switches Q1-Q4 comprise FET switches (e.g., MOS FETs) that can be switched on or off via a controller such as the controller 114 shown in FIG. 2. In some embodiments, transformer 132 is a cardiac floating (CF) grade isolation transformer.

The controller 114 activates the switches Q1-Q4 to control the current applied to the primary winding 130 to induce a voltage on the secondary windings 134 of the transformer 132. The controller 114 switches the switches Q1-Q4 at a switching frequency much greater than the frequency of the AC power from the AC power source 108. In some embodiments, the switching frequency is greater than about one hundred kilohertz (kHz) and may be up to several megahertz (MHz). In some embodiments, the switching frequency may be any frequency greater than 60 Hz. For example, the switching frequency may be 5 kHz or 10 kHz in some embodiments. The voltage induced on the transformer 132 generates a current which flows through diode D1 or D2 (according to the polarity of the voltage on the secondary windings 134) and is output to a wave-shaping filter 133 formed by inductor L and capacitor C. The diodes D1 and D2 may be actual diodes, synchronously controlled switches, or any other suitable component. The DC voltage output from the isolated DC/DC converter stage 128 is less than the DC voltage input to the isolated DC/DC converter stage, and the output of the isolated DC/DC converter stage is input to the DC/AC inverter 112, which generates an AC output for provision to the loads 106 (not shown in FIG. 3). In this embodiment, components of the AC/DC converter 110 and DC/AC converter 112 operate relative to a floating reference point that is different from a ground of AC power source 108.

Figure 4:
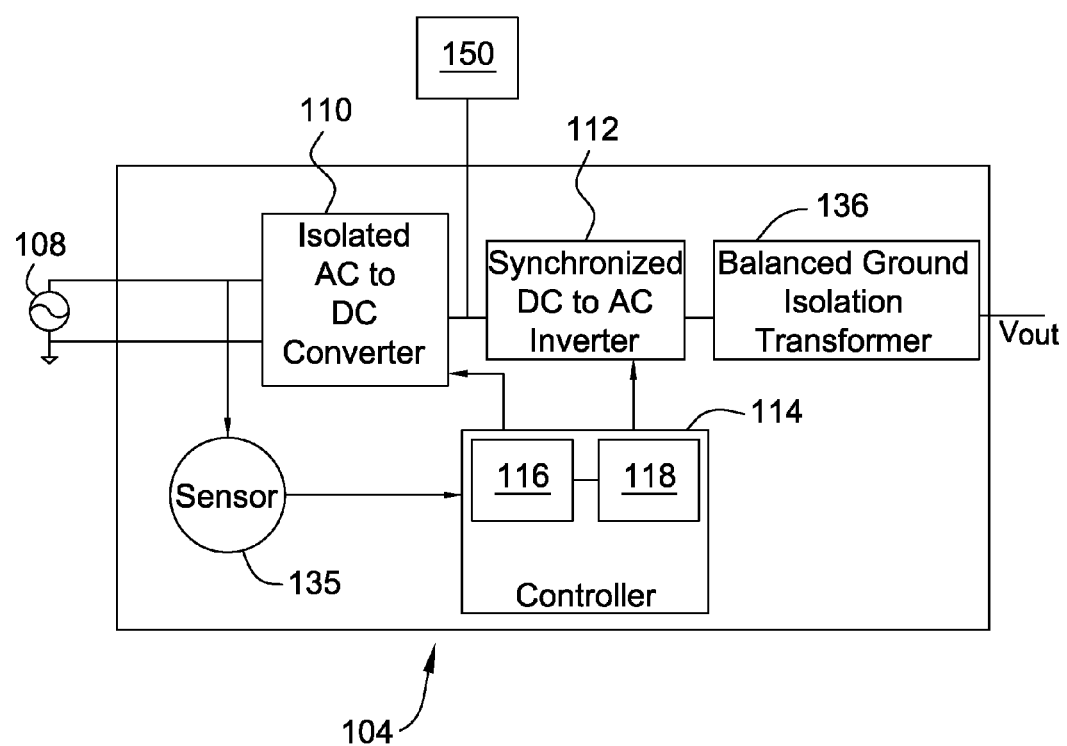
FIG. 4 is a diagram of another embodiment of a power supply for use in the medical system shown in FIG. 1.

Referring now to FIG. 4, there is shown a diagram of another exemplary power supply 104. The isolated AC/DC converter 110 receives the AC input from the AC source 108 and provides a DC output to the DC/AC converter 112. In this embodiment, the DC output also powers one or more DC loads 150. Although not explicitly shown, other embodiments may also include DC loads 150. The power supply 104 includes at least one sensor 135 coupled to the input of the power supply 104. The controller 114 receives the output of the sensor 135. The controller 114 monitors the frequency of the AC input voltage via the sensor 135 and operates the DC/AC converter 112 to produce an AC output with the same frequency as the AC power source 108. Thus, for example, the controller 114 will operate the DC/AC converter 112 to provide a 50 Hz AC output when the AC input is 50 Hz and to provide a 60 Hz AC output when the AC input is 60 Hz.

In the exemplary embodiment, the controller 114 monitors the phase of the AC input voltage via the sensor 135. To maintain an isolation barrier, the sensor 135 is an isolated sensor circuit. For example, in some embodiments, the sensor 135 is a galvanic isolation device, such as an optoisolator. Alternatively, the sensor 135 may be any device that facilitates monitoring the phase of the AC input voltage. In some embodiments, the controller 114 operates the DC/AC converter 112 to produce an AC output synchronized in phase with the AC input voltage. Alternatively, in other embodiments, the controller 114 operates the DC/AC converter 112 to produce an AC output that is not in phase with the AC input voltage, e.g., an output AC voltage that is 180 degrees out of phase with the AC input voltage.

As shown in FIG. 4, and in some embodiments, the output of the DC/AC converter 112 is provided to a balanced ground isolation transformer 136. Although discussed in conjunction with the embodiment shown in FIG. 4, the balanced ground isolation transformer 136 could be implemented within other embodiments described herein. The output ground is not connected to the ground on the input side power supply 104, but is instead a floating reference point. The isolation transformer 136 reduces noise (e.g., switching/chopping noise, etc.) that may otherwise be present on the AC output voltage from the power supply 104. Although shown as a component of the power supply 104, the isolation transformer 136 may be a component separate from the power supply 104 and may be located on the input or the output side of the power supply 104.

Figure 5:
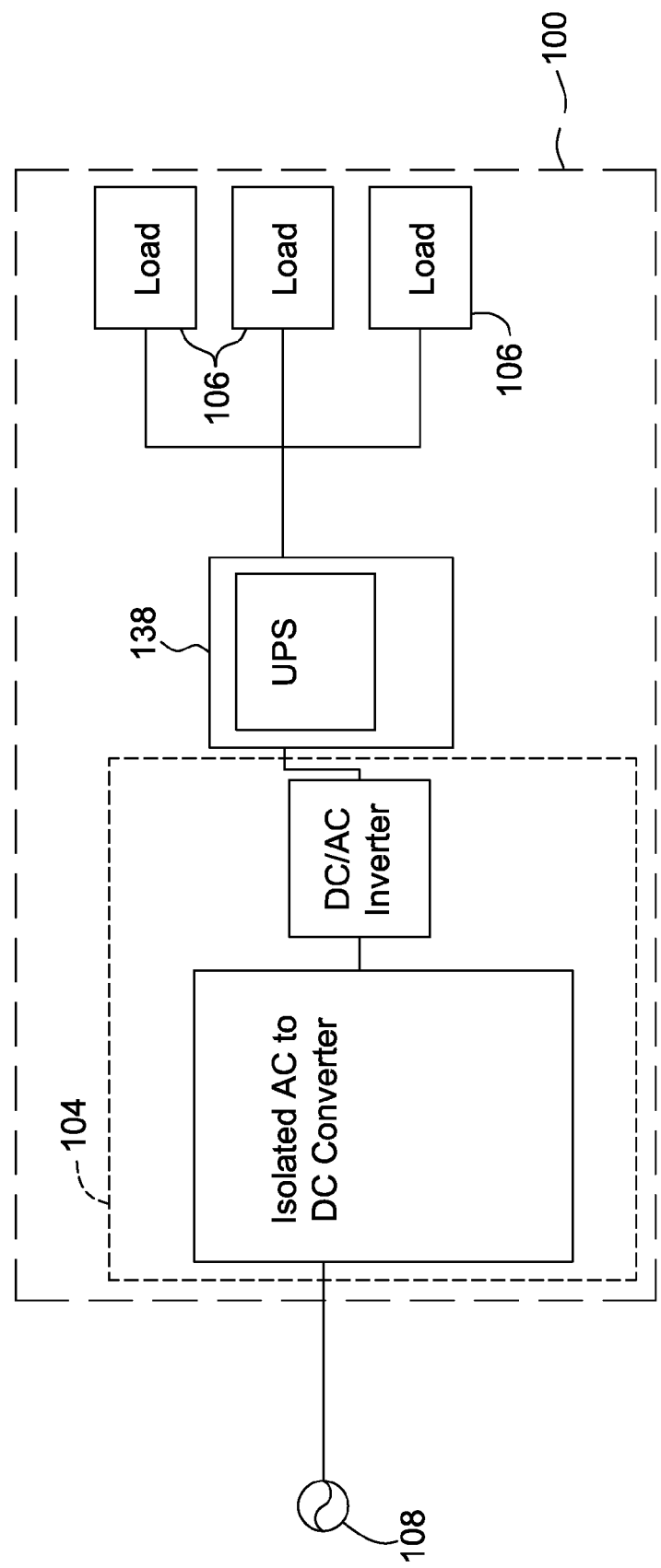
FIG. 5 is a block diagram of an embodiment of a medical system according to the present disclosure.

In some embodiments, the medical system 100 may include an uninterruptible power supply (UPS). FIG. 5 is a diagram of an exemplary embodiment of the medical system 100 that includes a UPS 138. The output of the power supply 104 passes through the UPS 138 to the loads 106. In other embodiments, the UPS 138 may be a part of the power supply 104. Moreover, the UPS 138 may be located on the input or the output sides of the power supply 104. During normal operation, the AC power output from the power supply 104 passes through the UPS 138 to the loads 106. The UPS includes a rechargeable battery (not shown) that is charged during such operation. When AC power is interrupted (e.g., during a power failure), the UPS 138 provides power to loads 106 by converting the DC power stored in the battery to AC power to supply the loads 106. In other embodiments, UPS 138 is coupled between the AC power source 108 and the input of the power supply 104 and functions in a similar manner.

Figure 6:
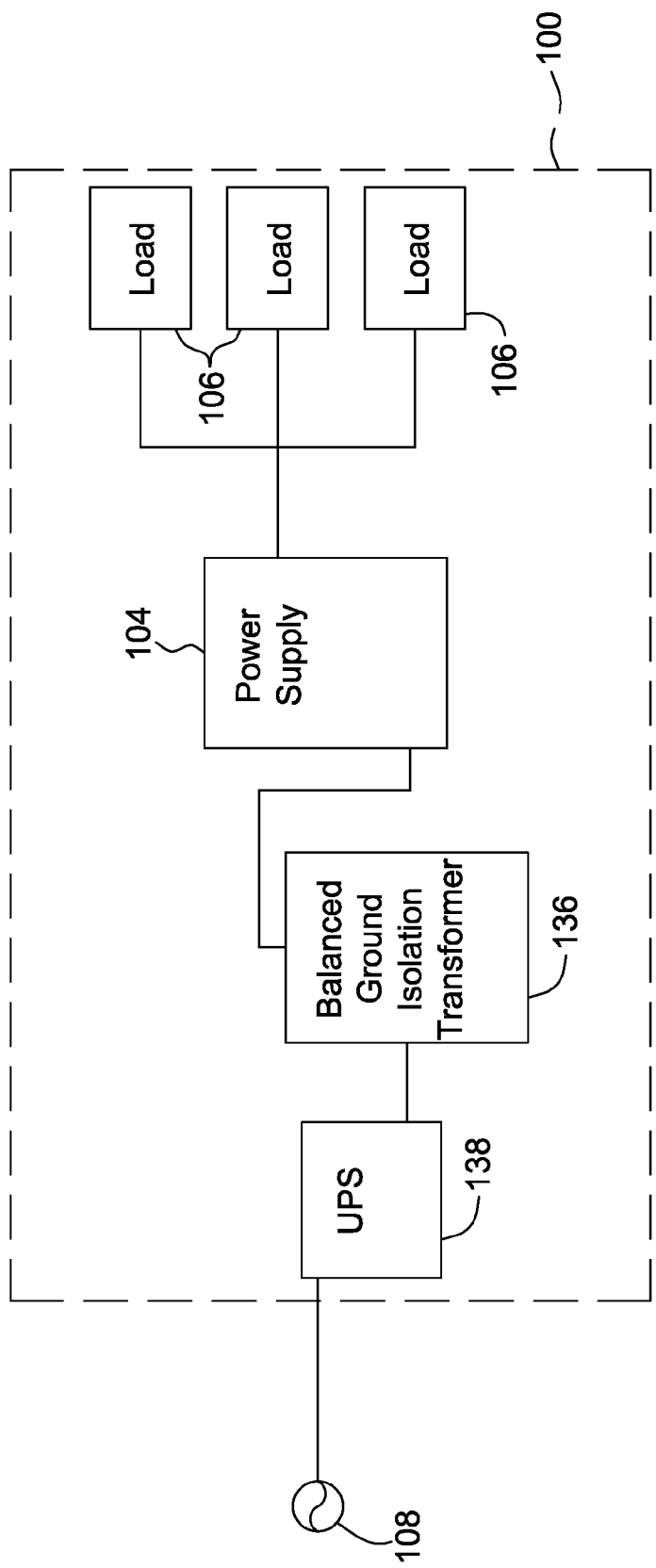
FIG. 6 is a block diagram of another embodiment of a medical system according to the present disclosure.

FIG. 6 is another embodiment of the medical system 100, including an AC power source 108, a UPS 138, and a balanced ground isolation transformer 136. In this embodiment, the UPS 138 and the transformer 136 are located on the input side of the power supply 104. The output of the power supply 104 is coupled to the loads 106 to provide operational power to the loads 106.

Figure 7:
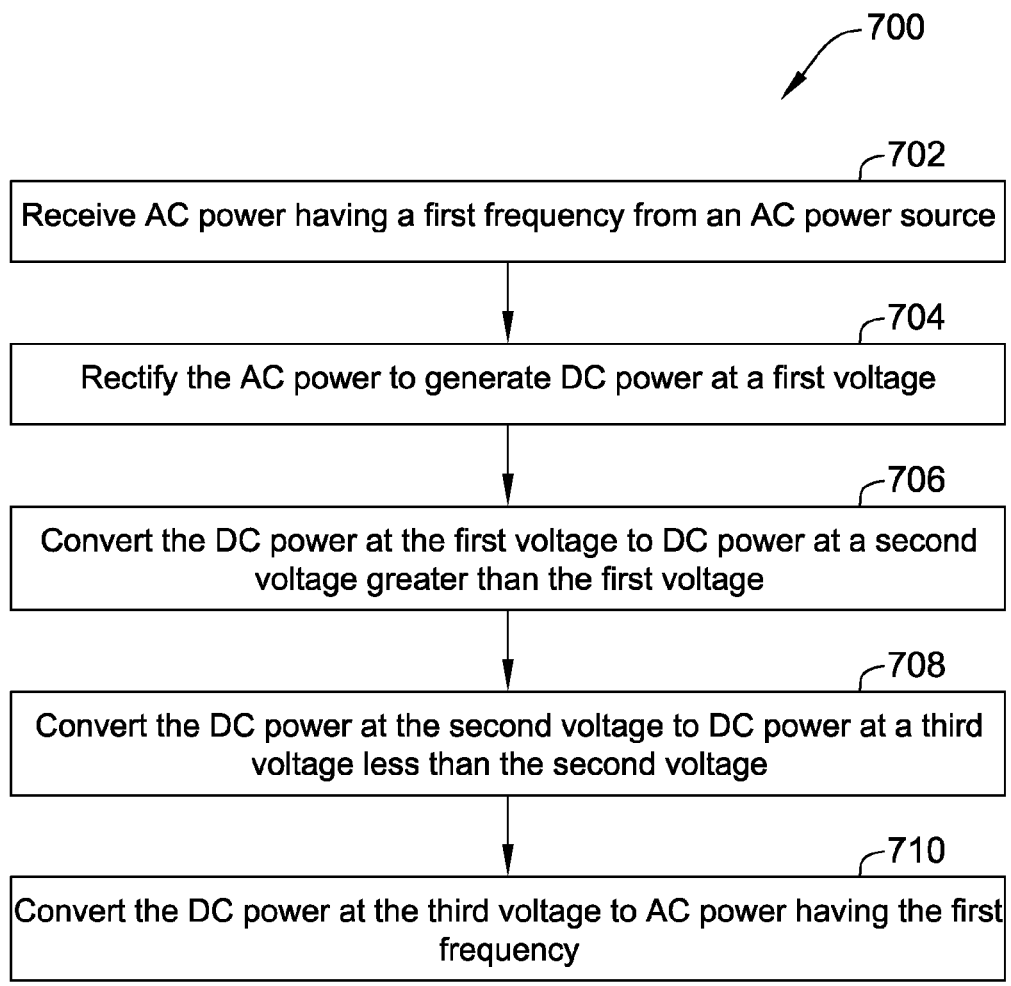
FIG. 7 is a flow diagram of a method for supplying alternating current (AC) power to a plurality of medical devices according to the present disclosure.

FIG. 7 is a flow diagram of a method 700 for supplying AC power to a plurality of medical devices. AC power having a first frequency is received 702 from an AC power source, such as the AC power source 108 shown in FIGS. 1-6. The AC power is rectified 704 to generate DC power at a first voltage. The DC power at the first voltage is converted 706 to DC power at a second voltage that is greater than the first voltage.

Using an isolated DC to DC power converter (e.g., the isolated DC to DC power converter 128 shown in FIG. 3) operating a switching frequency greater than the first frequency, the DC power at the second voltage is converted 708 to DC power at a third voltage that is less that the second voltage. In some embodiments, the isolated DC to DC power converter includes at least one transformer, and is one of a full bridge converter, a half bridge converter, a flyback converter, a forward converter, an active clamp forward converter, and a push-pull converter. The DC power at the third voltage is then converted 710 to an AC power output at the first frequency. The output AC power may have the same phase, or a different phase from the input AC power. In some embodiments the output AC power is delivered to the plurality of medical devices through a balanced ground isolation transformer, such as the balanced ground isolation transformed 136 shown in FIG. 4.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above without departing from the scope of the disclosure, it is intended that all matter contained in the above description and shown in the accompanying drawings shall be interpreted as illustrative and not in a limiting sense.

What is claimed is:

1. A medical system comprising:
   a plurality of medical devices; and
   a power supply configured to provide alternating current (AC) power to the plurality of medical devices, the power supply comprising:
   an input configured to receive AC power from an AC power source;
   an isolated switching power converter coupled to the input to receive the AC power and output AC power;
   a sensor coupled to the input and configured to generate a sensor output indicative of a first frequency of the AC power received from the AC power source;
   a controller coupled to the isolated switching power converter and the sensor, the controller configured to control, based on the sensor output, operation of the isolated switching power converter to output AC power at the first frequency; and
   an output coupled to the isolated switching power converter to provide the AC power output at the first frequency.

2. The medical system of claim 1 wherein the isolated switching power converter comprises:

an AC to direct current (AC/DC) converter stage coupled to the input and configured to output DC power; and a DC to AC (DC/AC) converter stage coupled to the AC/DC converter and configured to receive the DC power output from the AC/DC converter and output AC power.

3. The medical system of claim 2 wherein the AC/DC converter stage comprises:

a rectifier configured to rectify the AC power from the AC power source to DC power at a first voltage;

a boost converter configured to receive the DC power at the first voltage and output a DC power at a second voltage greater than the first voltage; and an isolated DC to DC (DC/DC) converter configured to receive the DC power at the second voltage and output a DC power at a third voltage.

4. The medical system of claim 3 wherein the controller is configured to operate the isolated DC/DC converter at a switching frequency greater than the first frequency and greater than about one hundred kilohertz.

5. The medical system of claim 3 wherein the sensor is a galvanic isolation device.

6. The medical system of claim 5 wherein the controller is configured to operate the DC/AC converter stage to output AC power at the first frequency with a same phase as the AC power from the AC power source.

7. The medical system of claim 5 wherein the controller is configured to operate the DC/AC converter stage to output AC power at the first frequency with a different phase than the AC power from the AC power source.

8. The medical system of claim 3 wherein the isolated DC/DC converter comprises a transformer, and wherein the isolated DC/DC converter is one of a full bridge converter, a half bridge converter, a flyback converter, a forward converter, an active clamp forward converter, and a push-pull converter.

9. The medical system of claim 1 further comprising a balanced ground isolation transformer coupled between the AC power source and the power supply.

10. The medical system of claim 1 further comprising an uninterruptable power supply (UPS) coupled to the power supply, wherein the UPS comprises a battery and a DC/AC converter configured to convert DC power from the battery to an AC power output.

11. The medical system of claim 1 wherein the plurality of medical devices comprise a cardiac mapping system, a cardiac stimulator, and an electrophysiology recording system.

12. The medical system of claim 1 wherein the system has a single fault condition leakage current of less than fifty microamperes.

* * * * *